US00PP24274P2

(12) United States Plant Patent
Knosher

(10) Patent No.: US PP24,274 P2
(45) Date of Patent: Feb. 25, 2014

(54) ***SALVIA* PLANT NAME 'BALYRICOSE'**

(50) Latin Name: *Salvia×sylvestris*
Varietal Denomination: Balyricose

(75) Inventor: Lynne Knosher, Campton Hills, IL (US)

(73) Assignee: Ball Horticultural Company, West Chicago, IL (US)

( * ) Notice: Subject to any disclaimer, the term of this patent is extended or adjusted under 35 U.S.C. 154(b) by 60 days.

(21) Appl. No.: 13/507,884

(22) Filed: Aug. 3, 2012

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Annette Para
(74) *Attorney, Agent, or Firm* — Audrey Charles

(57) ABSTRACT

A new and distinct cultivar of *Salvia* plant named 'Balyricose', characterized by its medium rose-colored flowers, medium green-colored foliage, and moderately vigorous, upright-mounded growth habit, is disclosed.

1 Drawing Sheet

Latin name of genus and species of plant claimed: *Salvia×sylvestris.*

Variety denomination: 'Balyricose'.

BACKGROUND OF THE INVENTION

The present invention relates to a new and distinct cultivar of *Salvia* plant botanically known as *Salvia×sylvestris* and hereinafter referred to by the cultivar name 'Balyricose'.

The new cultivar originated in a controlled breeding program in Elburn, Ill. during November 2008. The objective of the breeding program was the development of *Salvia* cultivars having distinctive flower coloration with an upright-mounded growth habit.

The new *Salvia* cultivar is the result of cross-pollination. The female (seed) parent of the new cultivar is the proprietary *Salvia×sylvestris* breeding selection coded 72-3, not patented, characterized by its dark violet-blue colored flowers, medium green-colored foliage, and moderately vigorous, upright-mounded growth habit. The male (pollen) parent of the new cultivar is the proprietary *Salvia×sylvestris* breeding selection coded 72-2, not patented, characterized by its dark blue and white bicolored flowers, medium green-colored foliage, and moderately vigorous, upright-mounded to upright growth habit. The new cultivar was discovered and selected as a single flowering plant within the progeny of the above stated cross-pollination during June 2010 in a controlled environment in Elburn, Ill.

Asexual reproduction of the new cultivar by terminal stem cuttings since June 2010 in Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balyricose' as a new and distinct cultivar of *Salvia* plant:

1. Medium rose-colored flowers;
2. Medium green-colored foliage; and
3. Moderately vigorous, upright-mounded growth habit.

Plants of the new cultivar differ from plants of the female and male parents primarily in flower color.

Of the many commercially available *Salvia* cultivars, the most similar in comparison to the new cultivar is 'Pink Friesland', U.S. Plant Pat. No. 18,152. However, in side-by-side comparison, plants of the new cultivar differ from plants of 'Pink Friesland' in at least the following characteristics:

1. Plants of the new cultivar have a flower color different from and more purple than plants of 'Pink Friesland'; and
2. Plants of the new cultivar have more branches per plant than plants of 'Pink Friesland'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balyricose'. The plants were grown in 1-gallon pots for 8 months a greenhouse in Elburn, Ill.

DETAILED BOTANICAL DESCRIPTION

Figure 1:
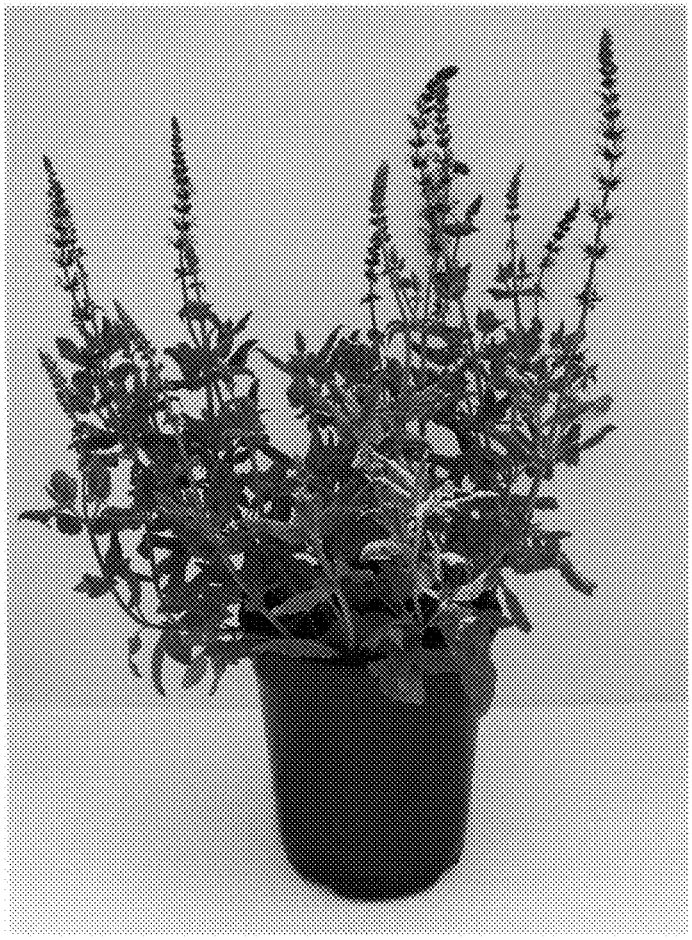
FIG. 1 illustrates a side view of the overall growth and flowering habit of 'Balyricose'.
Figure 2:
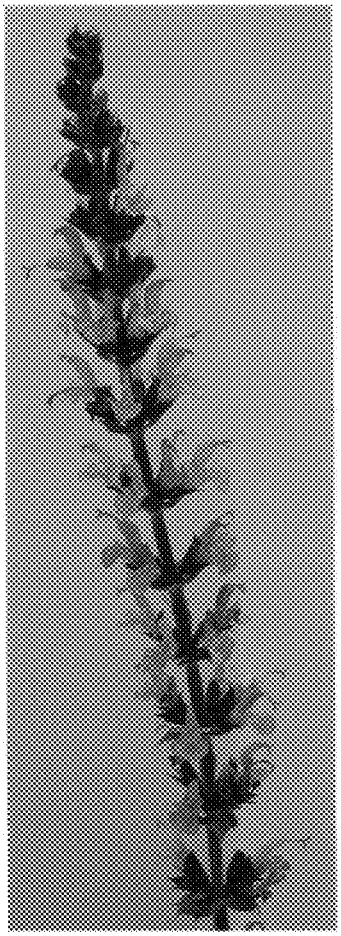
FIG. 2 illustrates a close-up view of an inflorescence of 'Balyricose'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2012 under natural light conditions in West Chicago, Ill.

The following descriptions and measurements describe plants produced from cuttings from stock plants and grown in a glass-covered greenhouse under conditions comparable to those used in commercial practice. The plants were grown in Elburn, Ill. in 1-gallon pots for 8 months utilizing a soilless growth medium. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Salvia×sylvestris* cultivar Balyricose.

Parentage:

*Female parent.*—Proprietary *Salvia×sylvestris* breeding selection coded 72-3, not patented.

*Male parent.*—Proprietary *Salvia×sylvestris* breeding selection coded 72-2, not patented.

Propagation:

*Type cutting.*—Terminal stem.

*Time to initiate roots.*—Approximately 9 to 12 days.

*Time to produce a rooted cutting.*—Approximately 24 to 28 days.

*Root description.*—Fine, fibrous white to dark brown in color.

*Rooting habit.*—Freely branching.

Plant description:

*Commercial crop time.*—Approximately 12 to 16 weeks from a rooted cutting to finish in a 15 cm pot.

*Growth habit and general appearance.*—Moderately vigorous, upright-mounded.

*Size.*—Height from soil level to top of plant plane: Approximately 38.5 cm. Width: Approximately 34.0 cm.

*Branching habit.*—Freely branching. Pinching enhances lateral branching. Quantity of branches per plant: Approximately 5 main basal branches and approximately 20 lateral branches.

*Branch.*—Shape: Square in cross section. Strength: Strong. Length to base of inflorescence: Approximately 16.5 cm. Diameter: Approximately 5.0 mm. Length of central internode: Approximately 4.5 cm. Texture: Densely pubescent with appressed, soft, short hairs. Color of young and mature stems: 138A to 138B with occasional speckles and streaks of 187A.

Foliage description:

*General description.*—Quantity of leaves per branch: Approximately 8. Fragrance: Strong, sage-like. Form: Simple. Arrangement: Opposite.

*Leaves.*—Aspect: Acute to perpendicular angle to stem. Shape: Ovate to elliptic. Margin: Crenate. Apex: Acute. Base: Obtuse to cordate. Venation pattern: Pinnate. Length of mature leaf: Approximately 6.5 cm. Width of mature leaf: Approximately 3.0 cm. Texture of upper and lower surfaces: Rugous, densely pubescent. Color of upper surface of young and mature foliage: 137A with venation of 145C. Color of lower surface of young and mature foliage: Closest 137C with venation of 145C.

*Petiole.*—Length: Approximately 1.5 cm. Diameter: Approximately 3.0 mm. Texture: Densely pubescent. Color: 145C.

Flowering description:

*Flowering habit.*—'Balyricose' is freely flowering under outdoor growing conditions blooming from spring through autumn and with limited flowering under short winter days in a greenhouse environment.

*Lastingness of individual floret.*—Approximately 4 to 5 days.

Inflorescence description:

*General description.*—Type: Spikes in verticillaster arrangement, florets in clusters of three, not persistent. Quantity of inflorescences per plant: Approximately 15. Fragrance: Faint, sweet. Length or height of inflorescence: Approximately 16.5 cm. Width of inflorescence: Approximately 2.0 cm. Quantity of fully-open flowers per inflorescence: Approximately 30 with up to 60 at peak flowering.

*Peduncle.*—Shape: Square in cross section. Strength: Strong. Aspect: Erect. Length: Approximately 3.5 cm. Diameter: Approximately 2.0 to 3.0 mm. Texture: Densely pubescent with appressed, soft, short hairs. Color: 138A to 138B.

Flower description:

*Type.*—Single, zygomorphic.

*Bud.*—Rate of opening: Generally takes 2 to 3 days for bud to progress from first color to fully open flower.

*Bud just before opening.*—Shape: Ovoid. Length: Approximately 5.0 mm. Diameter: Approximately 2.0 mm. Texture: Densely pubescent. Color: calyx of 144B with venation of 187A; petals of 77A.

*Corolla.*—Shape: Bilabiate, lower lip having three lobes, based fused. Width: Approximately 4.0 mm. Length: Approximately 1.1 cm. Depth: Approximately 7.0 mm.

*Upper lip.*—Shape: Hooded. Margin: Entire. Apex: Rounded. Length from throat: Approximately 5.0 mm. Width: Approximately 2.0 mm. Texture of inner surface: Glabrous. Texture of outer surface: Sparsely pubescent. Color of inner surface when first and fully open: Closest to 76C. Color of outer surface when first and fully open: N80D.

*Lower lip.*—Shape of central lobe: Orbicular, cupped. Shape of lateral lobes: Elliptic to oblong. Margin: Entire. Apex of central lobe: Emarginate. Apex of lateral lobes: Acuminate. Length from throat of central lobe: Approximately 4.0 mm. Width of central lobe: Approximately 4.0 mm. Length from throat of lateral lobes: Approximately 3.0 mm. Width of lateral lobes: Approximately 1.0 mm. Texture of upper surface: Glabrous. Texture of lower surface: Sparsely pubescent. Color of upper surface when first and fully open: N80B. Color of lower surface when first and fully open: N80C.

*Calyx.*—Shape: Tubular. Length: Approximately 5.0 mm. Diameter: Approximately 4.0 mm.

*Sepals.*—Quantity per flower: 5, fused. Shape: Elliptic. Apex: Acute. Length: Approximately 5.0 mm. Width: Approximately 2.0 mm. Texture of inner surface: Glabrous. Texture of outer surface: Densely pubescent. Color of inner surface: 137C. Color of outer surface: 144B with venation and margins of 187A.

*Bracts.*—Quantity: One bract located at the base of floret cluster. Length: Approximately 8.0 mm. Width: Approximately 7.0 mm. Texture: Glabrous with densely pubescent margins. Color of upper and lower surfaces: 137A with 187A at tip.

*Pedicel.*—Strength: Strong, flexible. Aspect: At an acute angle. Length: Approximately 1.0 mm. Diameter: Less than 1.0 mm. Texture: Densely pubescent. 187A.

*Reproductive organs.*—Androecium: Stamen quantity: 2 per flower, dorsifixed, strongly curved. Filament length: Approximately 3.0 mm. Filament color: NN155C, opaque. Anther shape: Narrowly elliptic to oblong. Anther length: Approximately 1.0 mm. Anther color: 200C. Pollen amount: None observed. Gynoecium: Pistil quantity: 1 per flower, strongly curved. Pistil length: Approximately 1.1 cm. Stigma shape: Cleft, two-parted. Stigma color: N80A. Style length: Approximately 9.0 mm. Style color: NN155D, opaque with an overlay of N80A that fades toward ovary. Ovary length: Approximately 1.0 mm. Ovary color: 144C.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Balyricose', substantially as herein shown and described.

* * * * *